US007817269B2

(12) United States Patent
Enderlein

(10) Patent No.: US 7,817,269 B2
(45) Date of Patent: Oct. 19, 2010

(54) HIGH RESOLUTION OPTICAL MICROSCOPY FEATURING FLUORESCENCE TRANSIENT MEASUREMENT

(75) Inventor: Jörg Enderlein, Berlin (DE)

(73) Assignee: PicoQuant GmbH, Berlin (DE)

(*) Notice: Subject to any disclaimer, the term of this patent is extended or adjusted under 35 U.S.C. 154(b) by 534 days.

(21) Appl. No.: 11/912,834

(22) PCT Filed: Apr. 28, 2006

(86) PCT No.: PCT/EP2006/004010

§ 371 (c)(1),
(2), (4) Date: Oct. 26, 2007

(87) PCT Pub. No.: WO2006/114329

PCT Pub. Date: Nov. 2, 2006

(65) Prior Publication Data

US 2008/0192262 A1    Aug. 14, 2008

(30) Foreign Application Priority Data

Apr. 28, 2005    (DE)    .................... 10 2005 020 202

(51) Int. Cl.
*G01J 3/30* (2006.01)
(52) U.S. Cl. ..................................... 356/318; 356/610
(58) Field of Classification Search ............... 356/317, 356/318, 610
See application file for complete search history.

(56) References Cited

U.S. PATENT DOCUMENTS 5,734,470 A * 3/1998 Rogers et al. ............... 356/502

FOREIGN PATENT DOCUMENTS

DE    102 39 028    3/2003
WO    WO 98/23941    6/1998

OTHER PUBLICATIONS

Schoenle et al.: Four-dimensional multiphoton microscopy with time-correlated single-photon counting, in: Applied Optics, vol. 39, Dec. 2000.
Becker et al.: High resolution TCSPC lifetime imaging, in: Proceedings of the SPIE, vol. 4963, Jan. 2003.

(Continued)

*Primary Examiner*—Tarifur Chowdhury
*Assistant Examiner*—Abdullahi Nur
(74) *Attorney, Agent, or Firm*—Ursula B. Day; Henry M. Feiereisen

(57) ABSTRACT

According to the invention, an excitation layer is focused into a sample and switched on suddenly in order to improve the microscopic resolution; the history of the resulting fluorescence transient is detected and imperatively depending on the excitation intensity, wherein different patterns for the history of different transients are determined for individual excitation intensity values and are matched with the measured transient and the amplitude of the pattern matching the excitation power in the focus is determined and used as a pixel value and the sample scanned in this manner, whereby the spatial resolution is improved to levels lying below the Abbe limit by evaluating the transient.

11 Claims, 4 Drawing Sheets

OTHER PUBLICATIONS

Krämer et al.: Fluorescence enhancement imaging (FLIM) based analysis of lipid organization in hepatocytes using the MicroTime 200, in: Picoquant application note, Feb. 2000.

Savitsky et al: Fluorescence enhancement of asCP595 is due to consecutive absorbance of two photons, in: SPIE-Int. Soc. Opt. Eng., vol. 5329, Jan. 2004.

Enderlein et al.: Fast fitting of multi-exponential decay curves, in: Optics Communications, vol. 134, Jan. 1997.

Schönle et al.: Far-field fluorescence microscopy with repetitive excitation, in: European Physical Journal, vol. 6, Jun. 1999.

Hell: Increasing the resolution of far-field fluorescence light miscroscopy by point-spread-function engineering, in: Plenum Press, 5$^{th}$ Edition, 1997.

Hell et al.: Concepts for nanoscale resolution in fluorescence microscopy, in: Current Opinion in Nuerobiology, vol. 14, 2004.

ML Gustafsson: Surpassing the lateral resolution limit by a factor of two using structured illumination microscopy, in: Journal of Microscopy, vol. 198, May 2000.

GL Gustafsson: Extended resolution fluorescence microscopy, in: Structural Biology, vol. 9, 1999.

Hell et al.: Properties of a 4Pi confocal fluorescence microscope, in: Optical Society of America, vol. 9, Dec. 1992.

Denk et al.: Two-photon laser scanning fluorescence microscopy, in: Science, vol. 248, Apr. 1990.

Richards et al.: Electromagnetic diffraction in optical systems. II. Structure of the image field in an aplanatic system, in: Proc. Royal Soc. London, 1959.

\* cited by examiner

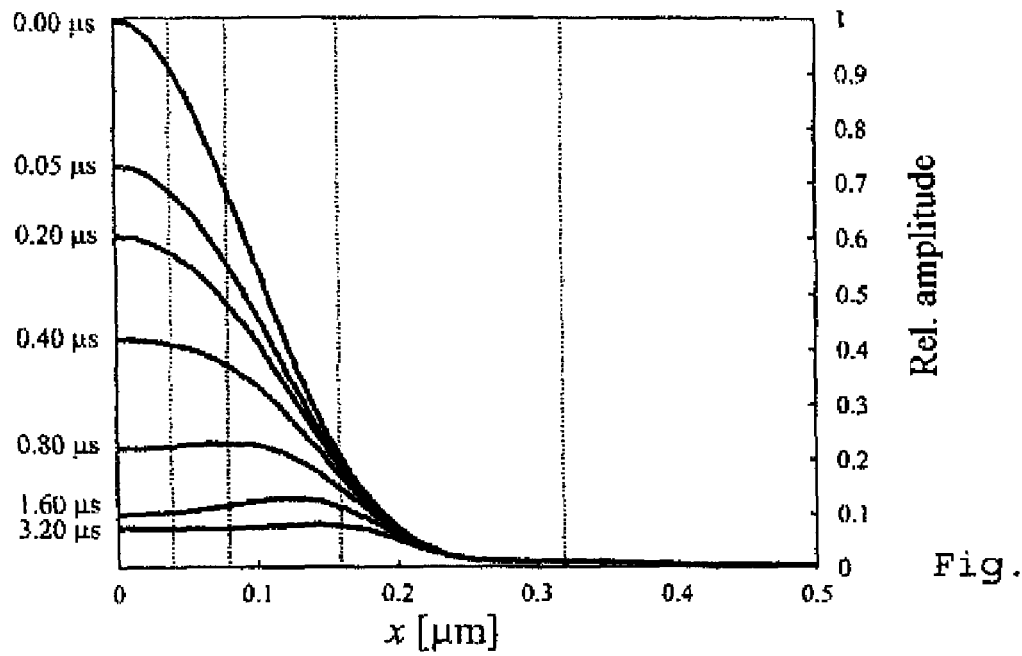
Fig. 2A
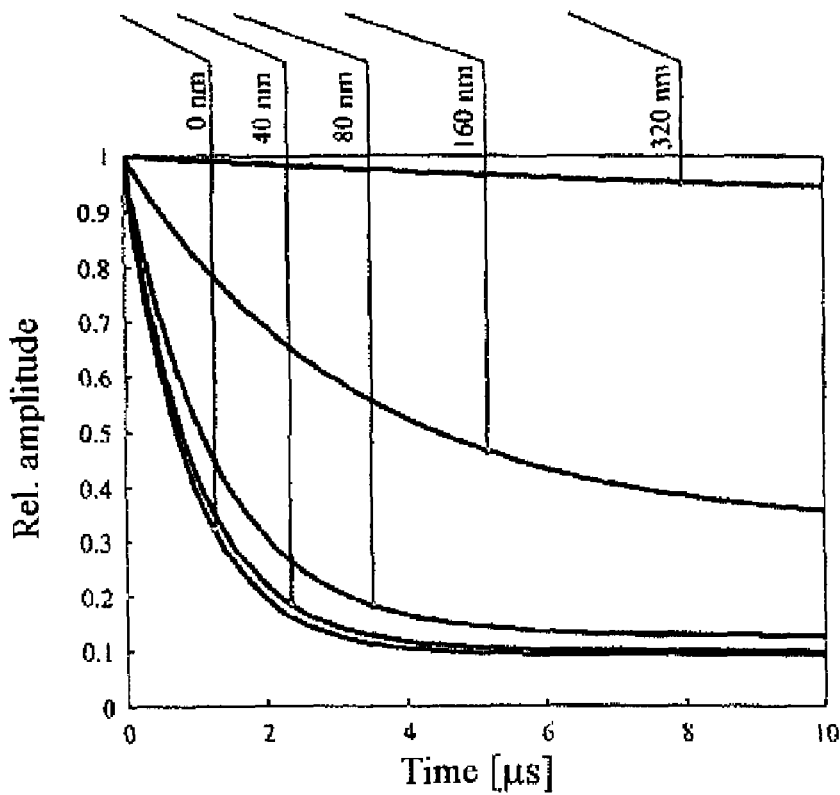
Fig. 2B
Fig. 2

HIGH RESOLUTION OPTICAL MICROSCOPY FEATURING FLUORESCENCE TRANSIENT MEASUREMENT

BACKGROUND OF THE INVENTION

1. Field of the Invention

Fluorescence microscopy is now an indispensable part of modern life sciences.

The essential limitation of fluorescence microscopy resides in its limited spatial resolution that is traditionally specified by the Abbe limit and lies at approximately 200 nm in the lateral direction.

2. Prior Art

Improving the spatial resolution of optical microscopy has long been the goal of many papers. The following approaches, inter alia, have been proposed:

- 4Pi Microscopy [S. W. Hell and H. K. Stelzer, J. Opt. Soc. Am. A 9, 2159 (1992)], in which two objects are used to focus oppositely directed excitation beams onto a sample.
- InM Microscopy which operates with spatially modulated light excitation [M. G. L. Gustafsson, J. Microsc. 198, 82 (2000)].
- One multiphoton excitation [W. Denk, J. H. Strickler and W. W. Webb, Science 248, 73 (1990)].
- RESOLFT, which uses nonlinear saturation effects [S. W. Hell, M. Dyba and S. Jakobs, Curr. Opin. Neurobiol. 14, 1 (2004)].
- STED (stimulated emission depletion) [S. W. Hell, in: *Topics in Fluorescence Spectroscopy*, 5$^{th}$ Edn., Edited by J. R. Lakowicz (Plenum Press, New York, 1997) pages 361-422].

An overview is to be found in [M. G. L. Gustafsson, Curr. Opin. Struct. Biol. 9, 627 (1999)].

OBJECT

It is an object of the invention further to improve the spatial resolution of microscopes.

ACHIEVEMENT

This object is achieved by means of the inventions having the features of the independent claims. Advantageous developments of the inventions are characterized in the subclaims. The wording of all the claims is hereby incorporated by reference in the content of this description.

It is a precondition for the applicability of the invention that in the event of a change in the excitation intensity the light signal S generated at a location of the microscoped sample has transients whose time profile is a function of the excitation intensity. It is therefore important for the invention to modulate the light excitation temporally.

Let us briefly consider the relationships at a given location of the microscoped sample. The temporary modulated excitation intensity A(t) can then be written generally as $$A(t)=a\alpha(t)$$

t being the time, $\alpha(t)$ being the normalized temporal modulation of the excitation, and a being the amplitude of the excitation. The signal generated by the sample on the basis of the excitation is likewise subdivided into normalized temporal modulation and amplitude, $$S(t)=s\sigma(t).$$

Were a strict linear relationship to exist between excitation and signal, $$S(t)=cA(t),$$

c being a constant dependent on the optical design and on the nature of the sample at the given location (sample characteristic), for example the concentration of a fluorescent dye, then the amplitudes of excitation and signal would be linearly proportional to one another, s=ca, and the normalized time modulation functions would be identical, $$\sigma(t)=\alpha(t).$$

It would therefore not be possible for the temporal modulation of the excitation to obtain from the signal amplitude s any additional separate gain in knowledge relating to the functions c and a. This statement that nothing can be learned of the spatial structure of the sample from the time response is also valid for the more general relationship $$S(t) = c \int_0^\infty dt'\, f(t') A(t-t')$$

with f as a response function independent of intensity (for example a fluorescence decay curve).

In the case of a general nonlinear relationship, however, $$S(t)=F[c,A(t)],$$

the general relationship $$\sigma(t)=G[c,a,\alpha(t)]$$

is obtained, inter alia, and so the temporal (normalized) modulation of the signal $\sigma$ becomes a function both of the excitation amplitude a and of the sample characteristic c.

Nothing can be learned of the spatial structure of the sample from the time response if a decomposition of G into the following parts:

$$G[c,a,\alpha(t)]=f(c,a)+g(c,a)\cdot h(\alpha(t))$$

exists. The desired information can be obtained only if h also depends on a, that is to say no such decomposition of G exists. h has, for example, the form of:

$$h(\alpha(t))=h(j(a)\cdot t)$$

in the preferred exemplary embodiments still to be outlined.

G always has the form of:

$$G[c,a,\alpha(t)]=c\cdot\{f(a)+g(a)\cdot h(j(a)\cdot t)\}$$

in these exemplary embodiments.

In every method of optical microscopy, the signal measured in the microscope by a detector (point detector or pixel on a camera, for example a CCD camera) is an integral over a region of space that is at least as large as the resolution limit of the microscope defined by the refraction of light. The last equation is then generalized to $$\sigma(t)\propto\int dr\, U(r) G[c(r),a(r),\alpha(t)],$$

U(r) being a function that describes the detection efficiency of the detector for light from the location r of the sample (for example the so-called point spread function in optics), and the integration being performed over the entire volume of the sample. The emboldened r stands for the three-dimensional position vector.

SUMMARY OF THE INVENTION

The core of the invention is to obtain by evaluating the temporal modulation σ(t) of the signal information relating to the sample characteristic c(r) with a spatial resolution that is below the diffraction-limited resolution determined by the function U(r).

Individual method steps are described in more detail below. The steps need not necessarily be carried out in the specified sequence, and the method to be outlined can also exhibit further steps not mentioned.

The following method is proposed for achieving the object:

In order to determine the spatial structure of an object, the first step is to select a suitable object in such a way that it contains at least one substance that can be excited to emit electromagnetic radiation by electromagnetic radiation, the distribution of this substance in the object being detected.

The spatial structure of an object, two-dimensional or three-dimensional, can be clarified by an appropriately spatially resolved image of at least parts of the sample. Here, in particular, electromagnetic radiation is light, that is to say electromagnetic radiation in the visible region.

Objects that can be excited to emit electromagnetic radiation by electromagnetic radiation are, for example, those marked with a dye. Typical examples are cells in which certain structural elements have been selectively visualized by dye marking, or which, for example, fluoresce of themselves. Here, an object can also be marked with a number of dyes that can be excited to emit with the same or different excitation wavelengths. Self-luminous substances, that is to say those that can be excited to emit without additional dye marking, further belong here.

The emission of electromagnetic radiation after electromagnetic excitation comprises all types of light scattering by molecules and/or objects, be this spontaneously, as in the case of Raman scattering, or with a delay, as in the case of fluorescence or phosphorescence, be it frequency shifted (inelastic) or at the excitation wavelength (elastic). Only the preferred embodiment, fluorescence, is explained in more detail below, as a rule without restriction of generality.

An excitation beam is coupled into the object in such a way as to yield a spatially inhomogeneous distribution of the excitation in the object. This can be achieved, for example, at the focus of a beam with a Gaussian distribution of the intensity distribution, or by a spatially modulated distribution of the excitation intensity, for example, by means of interference. A laser beam is used, in general, as excitation beam. In this case, only a single beam can suffice in advantageous refinements of the invention, and this requires an optical design that does not transcend what is usual.

The wavelength range of the excitation beam is selected in such a way that the excitation beam can excite the substance to emit.

The intensity of the excitation beam is changed so as to yield temporal transients of the emission of electromagnetic radiation by the substance. The excitation beam is typically firstly switched off and is switched on as quickly as possible at a given instant and left at a constant value for a given time. After, the excitation beam is switched off again and kept switched off for a given time such that a temporal rectangular pattern having on periods and off periods is yielded. As a rule, the emission is measured after the sudden switching on and during the on periods. Immediately after the sudden switching on, the emission exhibits temporally running transients until the setting up of a steady state that corresponds to the, for example, phasewise constant excitation power. In such an example, the on/off periods of the excitation beam are adapted to the lifetime of the fluorescent dye, for example: the on period is approximately equal to the fluorescence lifetime, while the off period is approximately 5 to 10 times longer such that it is possible to return all the molecules to the ground state before the next switching on.

Also possible, however, is another prescribed type of modulation of the intensity of the excitation beam which tracks the emission with the aid of a certain (transient) pattern if it is possible to infer from it the conclusions outlined below. A sinusoidal modulation of the excitation intensity, for example, is conceivable.

The substance and the wavelength range of the excitation are matched in such a way that after a change in the intensity of the excitation beam the temporal transients of the emission of electromagnetic radiation are a function of the respective spatial intensity of the excitation beam.

A temporal modulation of the excitation power at each location of the sample can also be achieved by a temporally variable spatial modulation of the excitation intensity, for example by a relative movement, taking place over time, of object and excitation focus.

For fundamental physical reasons, an excitation beam always has not only one wavelength, but always a specific distribution of wavelengths. Consequently, the talk here is of the wavelength range of the excitation. The formulation "excitation wavelength" always serves only as an abbreviated, simplifying designation.

The time profile of the transients is measured after a change in the intensity of the excitation beam, and specifically, advantageously beginning immediately after the change in the intensity of the excitation beam.

In the case of a (continuous) modulation of the intensity of the excitation beam, the emission is measured continuously, as a rule.

Just these transients are subsequently evaluated. To this end, different patterns for the time profile of different transients are determined for individual values of the excitation intensity. The patterns are adapted to the measured transient of the emission by means of different amplitudes, as a rule by a linear superposition or weighted addition of the patterns with different amplitudes to be adapted.

The amplitude is determined of that pattern which corresponds to the excitation power in a spatial region of interest. If the excitation beam is focused into a small region of interest (focus), the excitation power at the focus is highest, and the pattern of the transient is determined for the highest relevant excitation power. This is typically the fastest or slowest transient, depending on how the time profile of the transient depends on the excitation power.

This amplitude corresponds to the fluorescence signal that is generated at the location of highest excitation power, and is the inventive image signal for a given point. Consequently, the amplitude determined in such a way is taken as a measure of the concentration of the substance in the spatial region of interest. A pixel is thereby determined, for example.

The excitation beam is then coupled into the object in a spatially changed fashion until the spatial structure of at least parts of the object is determined. In other words, the object is scanned. Typically, the object or the focus is displaced for the purpose, and the method is repeated. However, it is also possible, for example, to displace the interference fringes.

The method uses conversion of temporal information into spatial information. The region of space thus read out is substantially smaller than the extent of the entire excitation intensity distribution. The method outlined achieves an at least four times better spatial resolution than conventional microscopy, that is to say far below the diffraction-defined so-called Abbe limit.

The Abbe limit can be undershot in principle with the aid of the inventive method. The principles involved cancel the limit derived by Abbe (under specific assumptions that no longer apply).

One possibility of matching the substance and the wavelength range of the excitation in such a way that after a change in the intensity of the excitation beam the temporal transients of the emission of electromagnetic radiation are a function of the respective spatial intensity of the excitation beam, consists in utilizing triplet state photophysics.

Another possibility of matching the substance and the wavelength range of the excitation in such a way that after a change in the intensity of the excitation beam the temporal transients of the emission of electromagnetic radiation are a function of the respective spatial intensity of the excitation beam, consists in using fluorescence while employing optical saturation of the excited state.

In this case, it is advantageous for measuring purposes to operate with fluorophores with a long fluorescence lifetime such that it is more easily possible to conduct temporal readouts of the rise in fluorescence after switching on the laser excitation. Possible candidates for consideration are fluorescent semiconductor nanocrystals (so-called quantum dots), diamond color centers, or stable dyes of long fluorescence lifetime such as, for example, europium-based or ruthenium-based dyes. All these fluorescent systems have fluorescence decay times of a few thousand nanoseconds to microseconds.

Two beams are used in an alternative approach to achieve the object.

Firstly, an excitation beam that is coupled into the object, which is specifically not necessarily spatially inhomogeneous, but also spatially homogeneous, if appropriate.

Secondly, at least a second beam. This is coupled to the object in such a way as to yield a spatially inhomogeneous distribution of the intensity of the second beam in the object.

The wavelength range of the excitation beam is selected in such a way that the excitation beam can excite the substance to emit. The wavelength range of the second beam is selected in such a way that the second beam can influence the emission of the substance. There are various possibilities to this end, and these are explained in individual exemplary embodiments and claims.

The intensity of the excitation beam is changed so as to yield temporal transients of the emission of electromagnetic radiation by the substance. Different variants are also perceivable here. In particular, the intensity of the excitation beam can be changed to yield pulses. Alternatively, it is temporally modulated, for example, sinusoidally.

The substance and the wavelength ranges of the beams are matched in such a way that after a change in the intensity of the excitation beam the temporal transients of the emission of electromagnetic radiation by the substance are a function of the respective spatial intensity of the second beam.

The procedure thereafter is essentially as in the first method outlined. The time profile of the transients is measured after a change in the intensity of the excitation beam, and specifically advantageously starting immediately after the change in the intensity of the excitation beam.

Emission is measured continuously as a rule in the case of a (continuous) modulation of the intensity of the excitation beam.

Different patterns for the time profile of different transients are determined. The patterns are adapted to the measured transient of the emission by means of different amplitudes.

The amplitude is determined of that pattern which corresponds to the intensity of the second beam in a spatial region of interest. The amplitude determined in such a way is taken as a measure of the concentration of the substance in the spatial region of interest. Finally, the beams are coupled into the object in a spatially changed fashion until the spatial structure of at least parts of the object is determined.

This method can use Förster resonance energy transfer (FRET) in an advantageous refinement. To this end, the substance selected is at least a pair consisting of a fluorophor (donor) and a quencher (acceptor) that execute Förster resonance energy transfer (FRET). The wavelength range of the excitation beam is selected in such a way that the excitation beam can excite the donor to emit. The wavelength range of the second beam is selected in such a way that the second beam can excite the acceptor into the level at which the donor outputs its energy. The acceptor is then blocked, and the decay time is correspondingly lengthened. This blocking, and therefore the decay time depend on the spatially inhomogeneous intensity of the second beam.

A further variant consists in using stimulated emission. To this end, the wavelength range of the second beam is selected in such a way that the second beam can effect a stimulated emission of the substance. This stimulated emission shortens the decay time. Moreover, it is a function of the spatially inhomogeneous intensity of the second beam, which can be used to raise the spatial resolution.

In the case of these two variants, the second beam is irradiated as a rule at constant intensity. However, it can also be modulated rectangularly, that is to say be switched on during excitation and the measurement period, but otherwise not. However, it is typical for the excitation beam to be irradiated in short pulses and highly repetitively, and for the second beam to be irradiated continuously.

The resolution can be raised yet further when the methods outlined are combined with other methods for raising resolution in microscopy, for example when the excitation of the sample by means of electromagnetic radiation is performed by means of a 4Pi microscope.

In order further to improve the signal-to-noise ratio, thus also the spatial resolution, a point can also be approached repeatedly so as to yield averaging over many cycles per pixel.

Instead of operating with only one focus, it is also possible to operate simultaneously with a number of foci, the result being to parallelize and accelerate the measurement.

Furthermore, the object is achieved by means of a computer program that executes the steps of the inventive method that can be executed by an arithmetic logic unit in one of its refinements when running on an arithmetic logic unit, a microcontroller, DSP, FPGA or computer, or on a plurality thereof in a network.

Furthermore, the object is achieved by a computer program having program code means for carrying out the steps of the inventive method that can be executed by an arithmetic logic unit in one of its refinements when the computer program is executed on an arithmetic logic unit, a microcontroller, DSP, FPGA or computer, or on a plurality thereof in a network. In particular, the program code means can be instructions stored on a computer-readable data medium.

Moreover, the object is achieved by a data medium on which there is stored a data structure that can execute the steps of the inventive method that can be executed by an arithmetic logic unit in one of its refinements after being loaded into a working and/or main memory of an arithmetic logic unit, a microcontroller, DSPs, FPGAs or a computer, or a plurality thereof in a network.

Again, the object is achieved by a computer program product having program code means stored on a machine-readable medium in order to carry out the steps of the inventive method that can be executed by an arithmetic logic unit in one of its embodiments when the program is executed on an arithmetic logic unit, a microcontroller, DSP, FPGA or computer, or on a plurality thereof in a network.

Here, the program of a computer program product is understood as a saleable product. It can basically be in any desired form such as, for example, on paper or a computer-readable data medium, or can, in particular, be distributed over a data transmission network.

Finally, the object is achieved by a modulated data signal that includes instructions for carrying out the steps of the inventive method that can be executed by an arithmetic logic unit in one of its refinements which instructions can be executed by an arithmetic logic unit, a microcontroller, DSP, FPGA or computer, or by a plurality thereof in a network.

Consideration is given as computer system both to a stand alone computer or microcontroller, DSPs or FPGAs, and to a network of microcontrollers, DSPs, FPGAs or computers, for example as an in-house, closed network, or else computers that are interconnected via the internet. Furthermore, the computer system can be implemented by a client/server constellation, parts of the invention running on the server, and others on a client.

Finally, the object is achieved by an apparatus that is suitable for carrying out the method outlined. The apparatus includes:

a) an electromagnetic radiation source for generating an excitation beam with a prescribed wavelength range; lasers, for example semiconductor lasers, are particularly suitable for this;

b) means for coupling the excitation beam into the object in such a way as to yield a spatially inhomogeneous distribution of the excitation in the object;

c) means for changing the intensity of the excitation beam; choppers, modulators, for example acoustooptic modulators (AOM), or a suitable electronic control of the radiation source, in particular when this is a semiconductor laser are suitable for this purpose;

d) means for measuring the time profile (transients) of the emission of the electromagnetic radiation by the object after a change in the intensity of the excitation beam; various types of temporarily satisfactory resolving detectors are suitable for this purpose in conjunction with a suitable electronic system for signal processing; there is typically a conversion of the optical signals into digital samples; these are processed algorithmically by dedicated or programmable hardware or microcontrollers or computers; in the case of the latter, this can be, for example, a DSP (digital signal processor) or an FPGA that generally digitize and process the measured values of the detector;

e) means for determining different patterns for the time profile of different transients for individual values of the excitation intensity;

f) means for adapting the pattern to the measured transient of the emission by means of different amplitudes; this is generally performed in an arithmetic logic unit which can be part of said electronic system;

g) means for determining the amplitude of that pattern which corresponds to the excitation power in a spatial region of interest;

h) means for selecting the amplitude determined in such a way as the measure of the concentration of the substance in the spatial region of interest; and i) means for coupling the excitation beam into the object in a spatially changed fashion until the spatial structure of at least parts of the object is determined.

An appropriate apparatus is required to carry out the method, which uses two beam. This apparatus has an electromagnetic radiation source for generating an excitation beam with a prescribed wavelength range. Furthermore, a second electromagnetic radiation source for generating a second beam with a prescribed wavelength range. Furthermore, means for coupling the excitation beam into the object, and means for coupling the second beam into the object in such a way as to yield a spatially inhomogeneous distribution of the second beam in the object.

Also required are means for changing the intensity of the excitation beam, as well as means for measuring the time profile (transients) of the emission of the electromagnetic radiation by the object after a change in the intensity of the excitation beam, and means for determining different patterns for the time profile of different transients. Added to this are means for adapting the patterns to the measured transient of the emission by means of different amplitudes, and means for determining the amplitude of that pattern which corresponds to the intensity of the second beam in a spatial region of interest.

Finally, the apparatus also has means for selecting the amplitude determined in such a way as the measure of the concentration of the substance in the spatial region of interest, and means for coupling the excitation beam into the object in a spatially changed fashion until the spatial structure of at least parts of the object is determined.

Further details and features emerge from the following description of preferred exemplary embodiments in conjunction with the subclaims. It is possible here to implement the respective features on their own or severally in combination with one another. The possibilities of achieving the object are not limited to the exemplary embodiments.

BRIEF DESCRIPTION OF THE DRAWING

The exemplary embodiments are illustrated schematically in the figures. Identical reference numerals in the individual figures in this case denote elements that are identical or have the same function or correspond to one another with regard to their functions. In detail:

FIG. 2 shows the time profile of the fluorescence signal at various positions of a Gaussian excitation curve;

FIG. 2A shows the time profile of the spatial fluorescence profile;

FIG. 2B shows the temporal fluorescence decrease for various positions outside the centre of the focus;

DETAILED DESCRIPTION OF PREFERRED EMBODIMENTS

Exemplary Embodiment 1

Figure 1:
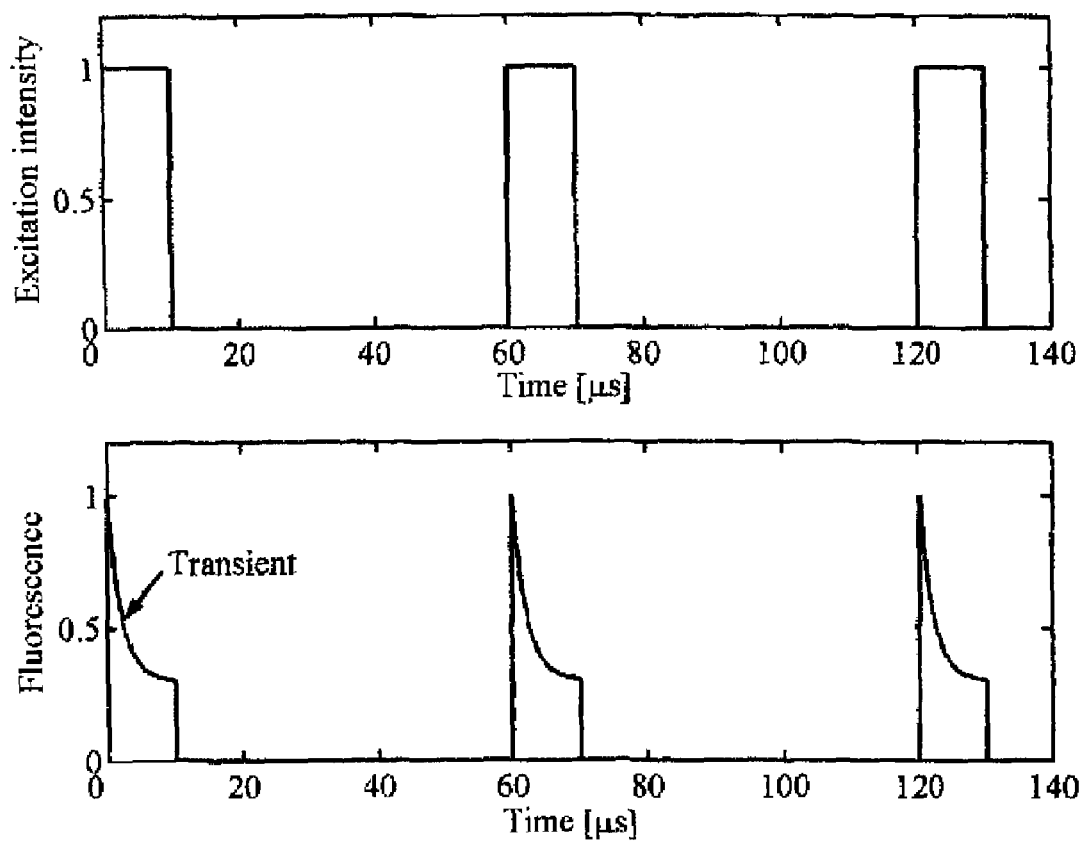
FIG. 1 shows a schematic of the time profile of the excitation intensity and of the fluorescence signal.

Confocal Fluorescence Microscopy Using Triplet State Photophysics

A confocal laser scanning fluorescence microscope is used as microscopy measurement system. The excitation is performed with the aid of a diffraction limited focused laser.

However, the excitation is not performed with constant excitation power, and the sample is not continuously scanned; however, with the laser switched off the optical system is fixedly focused onto a point on the sample, then the laser is switched on for a few microseconds and switched off again, then the optical system is moved to the next point in the sample, and the entire process is repeated until a complete image is recorded.

The on/off periods of the excitation laser are adapted in this exemplary embodiment to the lifetime of the triplet state: the on period is approximately equal to the triplet state lifetime (frequently a few microseconds), while the off period is approximately 5 to 10 times longer so that when switching on is next performed all the molecules have been able to return to the ground state.

It is preferably the fluorescence signal that is measured, and not the phosphorescence signal. The defected fluorescence signal is detected from each point approached with a high temporal resolution such that in the final analysis the time profile of the fluorescence signal is measured for each pixel approached during the on period after the laser has suddenly been switched on.

In the switched-off state of the laser, waiting is performed between two on periods of the excitation light until all the fluorescing molecules in the sample have again been able to return to the ground state. Alternatively, the sample can be scanned at large spatial intervals (large point spacings for which the laser foci do not overlap one another), and the scan is repeated several times in a slightly displaced fashion in order finally to achieve the desired spatial density at scanned points.

Fundamentally, during the complete measurement the distance between individual points approached should be at most as great as the spatial resolution that can be achieved with the aid of the method outlined, for example 40 nm. Depending on application, substantially smaller spatial distances will be selected between the individual points of the scan, for example 2.5 nm.

Many fluorescence dyes exhibit more or less pronounced triplet state photophysics. To this end, consideration is given to a molecule with a ground state $S_0$, an excited state $S_1$ and a triplet state $T_1$. It is assumed that the transition rate from the excited state to the ground state, the inverse of the fluorescence lifetime $\tau$, is substantially greater than the transition rate from the excited state to the triplet state, which is denoted as intersystem crossing rate $k_{isc}$. The following equations include appropriate instances of disregard.

If a fluorescing molecule is illuminated with a spatially inhomogeneous intensity distribution, the spatially dependent probability $s(r)$ of finding the molecule in the ground state or excited state is yielded from the solution of the kinematic equation $$\frac{ds(r,t)}{dt} = \frac{\tau a(r) k_{isc}}{1+\tau a(r)} s(r,t) + k_{ph}[1 - s(r,t)]$$

$a(r)$ being the spatially dependent rate of excitation of the molecule, that is to say the probability of making this transition from ground state to the excited state per time unit. $a(r)$ is given by $$a(r) = \frac{I(r)\sigma}{h\nu_{ex}}$$

$\sigma$ here being the effective absorption cross section of the molecule at the excitation wavelength $\nu_{ex}$, which is linked to the extinction coefficient by the relationship $$\sigma[cm^2] = 10^3 \ln 10 \epsilon [1 \times cm^{-1} \times mol^{-1}]/N_A,$$

$N_A$ being the Avogadro constant. h is the Planck constant and $I(r)$ is the spatially dependent intensity of the excitation beam at the excitation wavelength. $k_{ph}$ is the inverse lifetime of the triplet state, that is to say the phosphorescence rate.

If the exciting laser light is switched on suddenly at the instant $t=0$, and if all the molecules are in the ground state at this instant, that is to say if $s(r,t=0)=1$, the explicit solution of this equation is therefore given by:

$$s(r,t) = \frac{k_{ph}}{k_{ph} + \tau k_{isc} f(r)} + \frac{\tau k_{isc} f(r)}{k_{ph} + \tau k_{isc} f(r)} \exp\{-[k_{ph} + \tau k_{isc} f(r)]t\}$$

In this case, $f(r)$ stands for $$f(r) = \frac{a(r)}{1 + \tau a(r)}$$

The derived equation relates to a timescale, according to which so-called antibunching, that is to say the rapid rise in fluorescence after the laser is switched on, has decayed, and this lasts approximately exactly as long as the fluorescence decay time, as approximately between 1-10 ns. This means that the above equation is valid for times beyond the fluorescence decay time after suddenly switching on.

An example of the suddenly switched on excitation intensity and the fluorescence signal resulting therefrom is shown in FIG. 1.

After the laser is switched on, the measurable fluorescence signal from a point is then given by $$S(r,t) = \int dr' U(r-r') \left\{ \frac{c(r')k_{ph}}{k_{ph} + \tau k_{isc} f(r')} + \frac{c(r')\tau k_{isc} f(r')}{k_{ph} + \tau k_{isc} f(r')} \exp\{-[k_{ph} + \tau k_{isc} f(r')]t\} \right\},$$

given the following abbreviations: $U(r-r')$ is the point spread function (PSF) of the microscope, and $c(r)$ is the concentration distribution of the fluorescent dye in the sample.

The first, temporary constant, part of the signal $$S_0(r) = \int dr' U(r-r') \frac{c(r')k_{ph}}{k_{ph} + \tau k_{isc} f(r')}$$

is that which is measured and evaluated as useful signal in conventional microscopy with temporary constant excitation. By using the accurate knowledge of the PSF and of the excitation intensity distribution, that is to say, a(r), conventional microscopy can then attempt to obtain a better knowledge of the unknown function c(r) via deconvolution. However, the diffraction induced finite extent of the excitation a(r) will always be limiting.

In the case of the proposed method, a spatially better resolved knowledge of the function c(r) is obtained by evaluating the temporal change in the signal of the transient, that is to say by evaluating the temporal parts $$S_1(r,t) = \int dr' U(r-r') \frac{c(r')\tau k_{isc} f(r')}{k_{ph} + \tau k_{isc} f(r')} \exp\{-[k_{ph} + \tau k_{isc} f(r')]t\},$$

of the signal. As may be seen directly from the last equation, the temporary dependent fluorescence signal is a superposition of exponential decays, the rate of the exponential decay being a direct function of the excitation intensity, specifically $k_{ph} + \tau k_{isc} f(r)$.

This relationship is shown in FIG. 2, which shows the time profile of the fluorescence signal at various positions on a Gaussian excitation curve.

FIG. 2A shows the time profile of the spatial fluorescence profile on Gaussian laser excitation of the homogeneously distributed fluorophor. The photophysical parameters used are: fluorescence lifetime 1 ns triplet state lifetime 10 µs, intersystem crossing rate $10^8$/s. Acridine orange with an excitation wavelength of 470 nm and an emission wavelength of 530 nm was selected as dye. The power of the laser during the on period was 50 µW. The focusing was performed in diffraction limited fashion by an oil immersion objective with a numerical aperture of 1.4. The calculation of the distribution of the excitation power at the focus was performed in accordance with B. Richards and E. Wolf, Proc. Roy. Soc. London A 253, 358 (1959). The focus diameter at the center was approximately 180 nm. The power density or intensity at the focus was therefore 51 kW/cm². The effective absorption cross section is $2 \cdot 10^{-16}$ cm² at the excitation wavelength. This yields a maximum excitation rate a of 10 MHz at the center.

FIG. 2B shows the temporal fluorescence decrease for various positions outside the center of the focus, as indicated. The higher the excitation intensity, the quicker the molecules are pumped into the triplet state, and the quicker the fluorescence signal falls back to its steady state level.

The measured emission is the emission from the singulet state, that is to say the fluorescence. It can be detected selectively by filtering the wavelengths of the emitted light. Suitable dielectric bandpass filters are typically used to this end. Typical wavelengths for fluorescence signals of dyes are red shifted by approximately 20 to 100 nm with respect to the excitation wavelength.

The time profile of the measured fluorescence decay of each point is used to carry out a multiexponential fit, and the amplitude of the fastest component is determined. This amplitude corresponds to the fluorescence signal that is generated at the location of highest excitation power, and is the inventive image signal for a given point.

The conversion of temporal information into spatial information is thereby accomplished.

Figure 3:
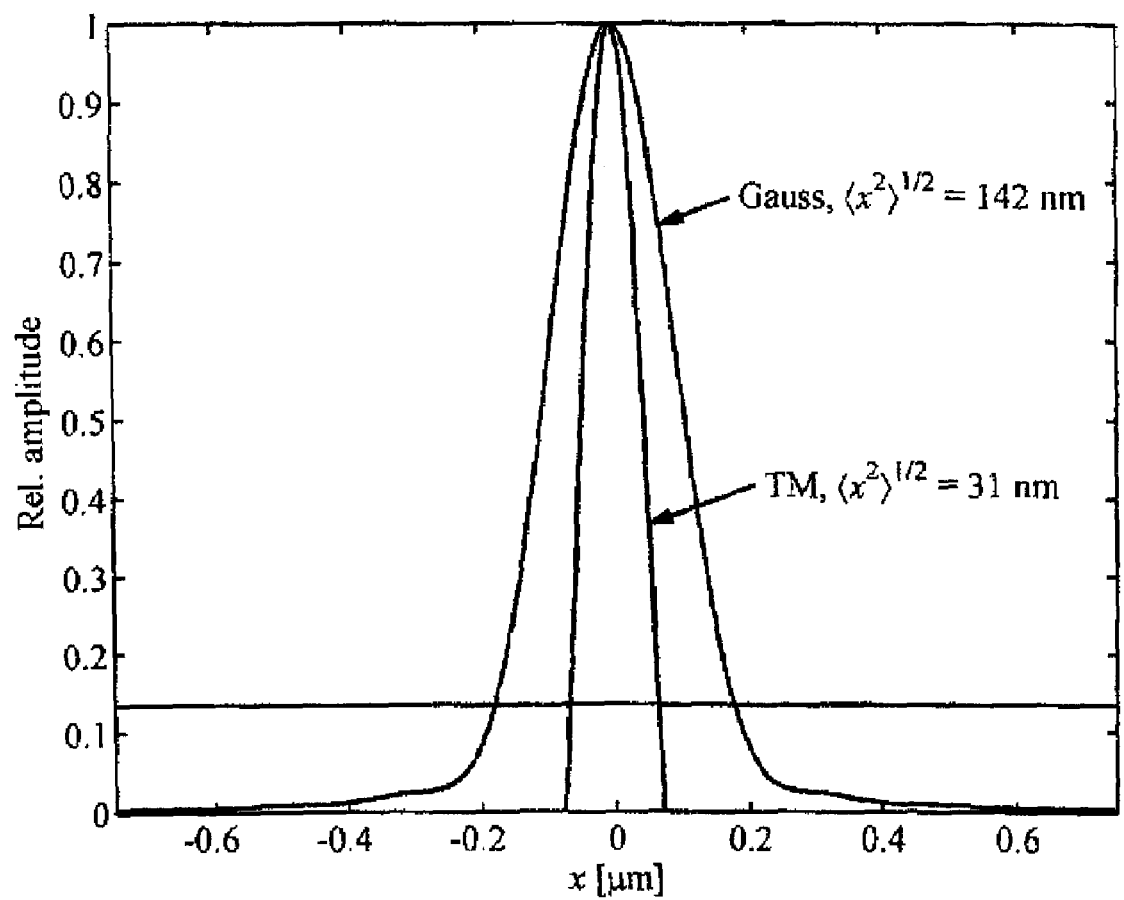
FIG. 3 shows the profile of the signal for perpendicular scanning of an infinitely narrow line distribution of a fluorescence dye.

The region of space thus read out is substantially smaller than the extent of the entire excitation intensity distribution. FIG. 3 illustrates this for a one-dimensional scan, the profile of the signal for vertical scanning being shown against an infinitely narrow line distribution of a fluorescence dye. FIG. 3 compares the spatial resolution of the proposed method and the steady state fluorescence intensity for vertical scanning of a Gaussian excitation against an infinitely narrow line of a fluorescing substance. The wider curve corresponds directly to the Gaussian profile of the excitation, and determines the spatial resolving power of conventional microscopy. The narrow curve corresponds to the profile of the imaging signal depicted here, the amplitude of the fastest fitted component. Also shown are the $1/e^2$ widths of the distributions (horizontal line giving a relative amplitude of $1/e^2 = 0.13$).

It is assumed in this example that the laser is switched on for 3.2 µs per pixel. After being switched on the laser was switched off during a period ten times the on period, that is to say for 32 µs.

The fluorescence intensity was measured in six time windows of different widths. The time intervals lay between the times 0, 0.05, 0.1, 0.2, 0.4, 0.8, 1.6 and 3.2 µs in a logarithmically graded fashion. The time intervals were selected correspondingly in order to reduce the data volume without losing decisive information.

The time profile of the intensity measured per pixel was fitted to the decay durations 0.75 and 1.5 µs by a biexponential decay. The imaging signal is the amplitude of the fast component (0.75 µs).

It is to be seen in FIG. 3 that the outlined method (line with the designation "TM", TM standing for transient microscopy) achieves an approximately five times better spatial resolution than conventional microscopy (line with the designation "Gauss"), that is to say far below the diffraction defined so-called Abbe limit. To this end, the intensity distribution widths and the root of the mean value of the position square $x^2$ weighted with the intensity distribution are also specified in FIG. 3 for the respective curves.

Exemplary Embodiment 2

Confocal Fluorescence Microscopy Using Optical Saturation of the Excited State

The measurement system is identical to that described in the first exemplary embodiment. However, the on/off periods of the excitation laser are now adapted to the lifetime of the fluorescence dye: the on period is approximately equal to the fluorescence lifetime, while the off period is approximately 5 to 10 times longer such that virtually all the molecules have been able to return to the ground state before the next switching on.

The excitation power should be so large that a distinct optical saturation of the excited state, or a distinct depletion of the ground state results at the excitation maximum. The measurable fluorescence signal is then known immediately after the excitation light is switched on, and over the duration of said light by:

$$S(r,t) = \int dr' U(r-r')c(r')f(r')\{1-\exp\{-[\tau^{-1}+f(r')]t\}\}$$

with the same abbreviations as in the first exemplary embodiment. It is to be seen that the quicker a steady state of the fluorescence is set up, the stronger the excitation intensity. In the steady state, at any time exactly as many molecules return to the ground state as are pumped into the excited state. It is only at the very beginning of the on period that all the molecules are in the ground state.

Again, the signal consists of a temporary constant term and a term, this time rising, that is time dependent, but now on the timescale of the fluorescence lifetime. The time dependent term is again the superposition of exponential functions, the exponential rate being dependent on the excitation intensity. It can be evaluated very similarly to the first exemplary embodiment, and can be used to improve the spatial resolution.

Exemplary Embodiment 3

Confocal Fluorescence Microscopy with Two Color Excitation Using Förster Resonance Energy Transfer The measurement system is identical to that described in the first exemplary embodiment, but the excitation is now performed with the aid of two lasers on two different wavelengths. Coupled pairs of dyes or other fluorescing substances (fluorophores) that execute efficient Förster resonance energy transfer (FRET) between a donor and an acceptor are used as signal transmitters.

The two excitation wavelengths efficiently excite the donor and the acceptor of the FRET pair. The acceptor can be excited continuously over time. The excitation brings the acceptor into just the state that could accept the energy of the donor. However, this is no longer possible after the excitation of the acceptor, the potentially accepting state is occupied, and the acceptor is blocked. The donor excitation again is performed discontinuously as in the preceding exemplary embodiments.

Only the donor fluorescence is measured, the acceptor can be a nonfluorescent quencher. $b(r)$ denotes the profile of unexcited acceptor molecules that is produced by the acceptor excitation. $b(r)$ in this case denotes the probability that an acceptor molecule at location r is not excited. $b(r)$ is a number between 0 and 1. $k_F$ denotes the FRET rate and its unit is 1/s. It is assumed that the FRET pairs are chemically coupled, that is to say an acceptor is always hanging on a donor, in the ratio of 1:1, and specifically in the same arrangement on average, such that the average FRET rate is the same for all FRET pairs. The measurable signal after once again switching on the laser in a step fashion is then given for the donor excitation by $$S(r,t) \approx \int dr' U(r-r') \frac{c(r')a(r')\{1-\exp[-(a(r')+k_F b(r')+\tau^{-1})t]\}}{1+\tau[a(r')+k_F b(r')]}.$$

In descriptive terms, the ground state is the starting point for all donor molecules. The more excitable acceptor molecules which can accept energy from a donor, that are there, the quicker the donor can be excited again. The physics is completely identical to the preceding exemplary embodiment, except that the excitation via FRET to the acceptor is now further added to the radiating excitation of the donor.

The advantage is that a measurable effect is obtained even when the excitation $a(r)$ is still very small so that it is still not possible to observe a distinct depletion of the ground state of the donor as in the previous exemplary embodiment. The dependents on excitation and location is achieved by the depletion of the ground state of the acceptor.

By contrast with the second exemplary embodiment, the excitation of the donor can be performed here far below the optical saturation intensity, $a(r) \ll \tau^{-1}$. The FRET rate $k_F$ should be large enough, and the acceptor should be pumped sufficiently strongly by the second laser into the state in which it can accept no energy from the donor. This procedure should function particularly well with long lived acceptors in the case of which the excited state can be effectively populated.

The signal that can be evaluated according to the invention, the time profile of the fluorescence, is then determined (neglecting $a(r)$) by the spatially dependent rate $\tau^{-1}+k_F b(r)$, that is to say on the timescale of the fluorescence lifetime. $b(r)$, the probability profile of nonexcited acceptor molecules, is smallest at the focus of the laser beam for the acceptor excitation, and so the longest donor fluorescence lifetime corresponds to the location of highest acceptor excitation (lowest probability $b(r)$ of nonexcited acceptors), and vice versa.

The proposed method now consists in fitting the fluorescence lifetime of the measured donor fluorescence at each point by reason of a multiexponential fit. The imaging signal is then the amplitude of the component with the longest lifetime. In this exemplary embodiment, the spatial resolution is dominated by the spatial profile of the acceptor excitation, but it is not limited or determined thereby. The limit of the spatial resolution is a fraction of the spatial resolution of the acceptor excitation.

Exemplary Embodiment 4

Confocal Fluorescence Microscopy with Two Color Excitation Using Stimulated Emission The measurement system is identical to that described in the first exemplary embodiment, but the excitation is now performed with the aid of two lasers on two different wavelengths. The first wavelength is used for the efficient fluorescence excitation of a fluorescing substance (fluorophor), while the second is used to excite the stimulated emission of the same substance. In this process, the light of the two wavelengths is focused into the sample with maximum spatial overlap, for example in that the light of the two wavelengths is guided to the objective through the same single mode optical fiber, is collimated by the same lens, and is then focused into the sample by the same objective. Furthermore, the fluorescence excitation is performed in short pulses with a high repetition rate such that the pulse lengths are distinctly smaller than the characteristic fluorescence decay time of the excited substance, and the spacing between pulses is considerably longer than this fluorescence decay time. The excitation at the wavelengths of stimulated emission takes place continuously, that is to say at constant intensity.

Alternatively, the fluorescence excitation can be performed with the aid of a modulated signal (with typical modulation frequencies in the region of MHz to GHz), and the detection of the fluorescence can be performed with the aid of a phase sensitive electronic system that determines the phase shift and the modulation level of the fluorescence emission in order to determine the decay time.

The fast decay of the fluorescence intensity after each fluorescence excitation pulse is measured, typically in the so-called single photon counting mode [see WO 98/23941 A2, for example], by making use of sufficiently fast single photon sensitive photoelectric detectors and electronic detection systems. The measurable signal after a fluorescence excitation pulse is then given by $$S(r, t) \approx \int dr' U(r-r')c(r')\sigma_{01} T_{pulse} I_{ex}(r')\exp\left\{-\left[\frac{1}{\tau} + \sigma_{SE} I_{SE}(r')\right]t\right\},$$

$\sigma_{01}$ being the effective absorption cross section at the excitation wavelength; $\sigma_{SE}$ being the effective cross section of the stimulated emission at the wavelength used for the stimulated emission; τ being the assumed monoexponential fluorescence decay time intrinsic to the substance; $T_{pulse} \ll \tau$ being the length of the light pulses used for fluorescence excitation; and $I_{ex}(r)$ and $1_{SE}(r)$ being the as far as possible identical spatial intensity profiles of the light used for the fluorescence excitation and for the stimulated emission (in photons per time per carrier). All other variables have the same significance as in the exemplary embodiment 1.

As in the exemplary embodiment 1, a spatially better resolved knowledge of the function c(r) is once again achieved by evaluating the temporal change in the signal of the transient, that is to say by evaluating the temporal part of S(r,t), now again on the timescale of the fluorescence lifetime. As may be seen directly from the last equation, the temporally dependent fluorescence signal is a superposition of exponential decays, the rate of the exponential decay being a direct function of the intensity of the emission of the light used that is to be stimulated, specifically $\tau^{-1} + \sigma_{SE} 1_{SE}(r')$.

Figure 4:
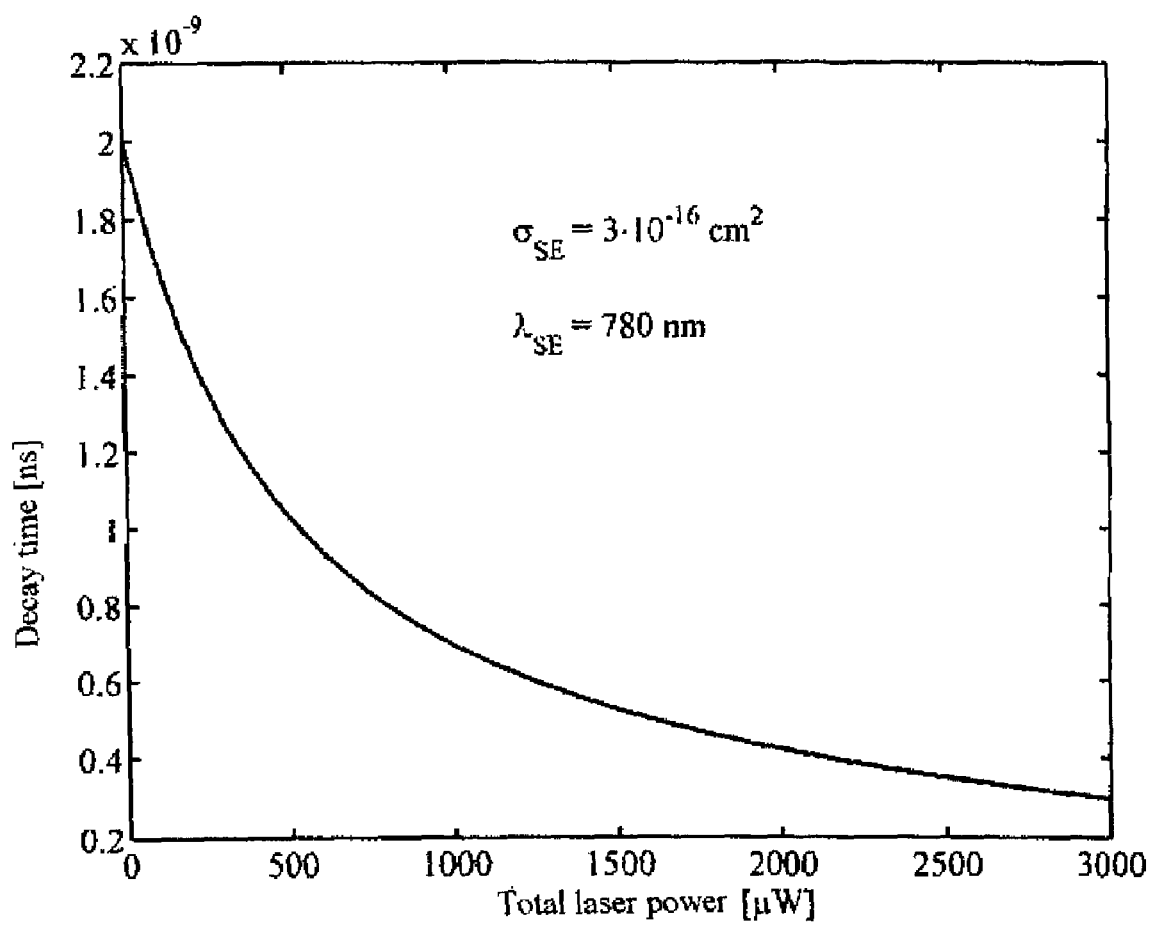
FIG. 4 shows the dependence of the delay time on the power of the laser used for a stimulated emission.

This relationship is shown in FIG. 4, which shows the decay time as a function of the power of the focussed laser used for the stimulated emission. An intrinsic fluorescence lifetime of 2 ns has been assumed for the fluorophor used, and it has been assumed that the laser used for the stimulation emission was focused onto a focus diameter of 400 nm at 780 nm wavelength, and an effective cross section of the stimulated emission was assumed at $3*10^{-16}$ cm$^2$.

The proposed method now consists in fitting the fluorescence lifetime at each point by means of a multiexponential fit. The imaging signal is then the amplitude (normalized or absolute) of the component with the shortest lifetime. In this exemplary embodiment, the spatial resolution is dominated by the spatial profile of the light used for the stimulated emission. The limit of the spatial resolution is a fraction of the spatial resolution of the light used for the stimulated emission.

A method for improving the spatial resolution in far field microscopy in which two different lasers are used for excitation is also proposed in the document Schönle, A., Hell, S. W.; "Far-field fluorescence microscopy with repetitive excitation"; Eur. Phys. J. D. Vol. 6, pages 283-290 (1999). In this case, an excitation laser irradiates in a pulsed fashion, while a second laser starts only after the pulse of the excitation laser and radiates for a prescribed short time in order to pump the molecules to a higher level, the result being to lengthen the decay time. This effect is a function of the spatial intensity of the second laser and can be used to improve the spatial resolution in far field microscopy. The emission is measured only after also switching off the second laser. The price of the higher spatial resolution is therefore a drastic signal loss. In this method, stimulated emission explicitly plays only a negligible role. Moreover, use is made of a completely different spectroscopic mechanism with the co-operation of a different energy level of the substance.

Exemplary Embodiment 5

4Pi Microscopy

The measurement system for this exemplary embodiment is a 4Pi microscope [S. W. Hell and H. K. Stelzer, J. Opt. Soc. Am. A 9, 2159 (1992)] as described in detail in the literature. Excitation, detection and signal evaluation are performed very similar to the first four exemplary embodiments. It is essential here that the inventive evaluation of the time profile of the measured fluorescence aimed at the inventive imaging signal detects only regions of space in which the excitation intensity lies above a certain limiting value, realistically at over 80% of the maximum excitation intensity at the focus center. Consequently, the fluorescence signal, which arises at the known secondary maxima of the excitation of a 4Pi microscope, exerts no influence on the inventive imaging signal.

Exemplary Embodiment 6

Far Field Fluorescence Microscopy with Spatially Modulated Excitation

In this exemplary embodiment, the fluorescence excitation is performed over a large area but in a spatially modulated fashion (for example by producing a grating on the sample), and the detection is performed with the aid of a camera that permits the tracking of temporally fast processes, for example with the aid of a gateable CCD camera using the Boxcar method. The fluorescence excitation is once again switched on in a step fashion for a short time and switched off again. When the detection is performed using the Boxcar method, a different time window of the fluorescence decay (or fluorescence rise, as in the second exemplary embodiment) is measured with the aid of a camera for each instance of switching on. The signal is then evaluated pixel by pixel very similar to the first four exemplary embodiments. The spatial resolution can be further improved by displacing or rotating the spatial modulation of the excitation.

LIST OF LITERATURE CITED

S. W. Hell and H. K. Stelzer, J. Opt. Soc. Am. A 9, 2159 (1992)
M. G. L. Gustafsson, J. Microsc. 198, 82 (2000)
W. Denk, J. H. Strickler and W. W. Webb, Science 248, 73 (1990)
S. W. Hell, M. Dyba and S. Jakobs, Curr. Opin. Neurobiol. 14, 1 (2004)
S. W. Hell, in: *Topics in Fluorescence Spectroscopy*, 5$^{th}$ Edn., Edited by J. R. Lakowicz (Plenum Press, New York, 1997) pages 361-422
M. G. L. Gustafsson, Curr. Opin. Struct. Biol. 9, 627 (1999)
B. Richards and E. Wolf, Proc. Roy. Soc. London A 253, 358 (1959) WO 98/23941 A2
A. Schönle, S. W. Hell: "Far-field fluorescence microscopy with repetitive excitation"; Eur. Phys. J. D. Vol. 6, pages 283-290 (1999)

What is claimed is:

1. A method for determining a spatial structure of an object by means of fluorescence spectroscopy, having the following steps: a) selecting the object in such a way that it contains at least one suitable substance that can be excited to emit electromagnetic radiation by electromagnetic radiation, the distribution of this substance in the object being detected; b) coupling an excitation beam into the object in such a way as to yield spatial regions with different excitation intensities in the object; c) selecting the wavelength range of the excitation beam in such a way that the excitation beam can excite the substance to emit; d) changing the intensity of the excitation beam so as to yield temporal transients of the emission of electromagnetic radiation by the substance; e) matching the substance and the wavelength range of the excitation in such a way that after a change in the intensity of the excitation beam the temporal transients of the emission of electromagnetic radiation are a function of the respective intensity of the excitation beam; f) measuring the time profile of the transients after a change in the intensity of the excitation beam; g) determining different patterns for the time profile of different transients for individual values of the excitation intensity; h) adapting the patterns to the measured transient of the emission by means of different amplitudes; i) determining the amplitude of that pattern which corresponds to the excitation intensity in said spatial region of interest, wherein the amplitude determined in such a way is taken as a measure of the concentration of the substance in the spatial region of interest; and j) coupling the excitation beam into the object in a spatially changed fashion until the spatial structure of at least parts of the object is determined.

2. The method as claimed in claim 1, wherein the substance and the wavelength range of the excitation are matched in such a way that after a change in the intensity of the excitation beam on the basis of triplet state photophysics the temporal transients of the emission of electromagnetic radiation are a function of the respective intensity of the excitation beam.

3. The method as claimed in claim 1, wherein fluorescence is selected as electromagnetic emission; and in that the substance and the wavelength range of the excitation are matched in such a way that after a change in the intensity of the excitation beam on the basis of the use of optical saturation of the excited state the temporal transients of the emission of electromagnetic radiation are a function of the respective intensity of the excitation beam.

4. The method as claimed in claim 1, wherein the excitation of the sample by means of electromagnetic radiation is performed by means of a 4Pi microscope.

5. The method as claimed in claim 4, wherein the excitation of the sample by means of electromagnetic radiation is performed by means of a 4Pi microscope.

6. A method for determining a spatial structure of an object by means of fluorescence spectroscopy, having the following steps: a) selecting in such a way that it contains at least one suitable substance that can be excited to emit electromagnetic radiation by electromagnetic radiation, the distribution of this substance in the object being detected; b) coupling an excitation beam into the object; b1) coupling at least one second beam into the object in such a way as to yield spatial regions with different excitation intensities the object; c) selecting the wavelength range of the excitation beam in such a way that the excitation beam can excite the substance to emit; c1) selecting the wavelength range of the second beam in such a way that the second beam can influence the emission of the substance; d) changing the intensity of the excitation beam so as to yield temporal transients of the emission of electromagnetic radiation by the substance; e) matching the substance and the wavelength ranges of the beams in such a way that after a change in the intensity of the excitation beam the temporal transients of the emission of electromagnetic radiation by the substance are a function of the respective intensity of the second beam; f) measuring the time profile of the transients after a change in the intensity of the excitation beam; g) determining different patterns for the time profile of different transients; h) adapting the patterns to the measured transient of the emission by means of different amplitudes; i) determining the amplitude of that pattern which corresponds to the intensity of the second beam in said spatial region of interest, wherein determining the amplitude in such a way that is taken as a measure of the concentration of the substance in the spatial region of interest; and j) coupling the beams into the object in a spatially changed fashion until the spatial structure of at least parts of the object is determined.

7. The method as claimed in claim 6, wherein
a) the substance selected is at least a pair consisting of a fluorophor (donor) and a quencher (acceptor) that execute Förster resonance energy transfer (FRET);
b) the wavelength range of the excitation beam is selected in such a way that the excitation beam can excite the donor to emit; and
c) the wavelength range of the second beam is selected in such a way that the second beam can excite the acceptor into the level at which the donor outputs its energy.

8. The method as claimed in claim 7, wherein the wavelength range of the second beam is selected in such a way that the second beam can effect a simulated emission of the substance.

9. The method as claimed in claim 6, wherein the second beam is irradiated at constant intensity.

10. An apparatus for determining a spatial structure of an object by means of fluorescence spectroscopy comprising: a) an electromagnetic radiation source for generating an excitation beam with a prescribed wavelength range; b) means for coupling the excitation beam into the object in such a way as to yield spatial regions with different excitation intensities in the object; c) means for changing the intensity of the excitation beam in such a way as to yield a temporal square pattern of switched-on and off periods; d) means for measuring the time profile (transients) of the emission of the electromagnetic radiation by the object during the switched-on period; e) means for determining different patterns for the time profile of different transients for individual values of the excitation intensity; f) means for adapting the pattern to the measured transient of the emission by means of different amplitudes; g) means for determining the amplitude of that pattern which corresponds to the excitation intensity in said spatial region of interest; h) means for selecting the amplitude determined in such a way as the measure of the concentration of the substance in the spatial region of interest; and i) means for coupling the excitation beam into the object in a spatially changed fashion until the spatial structure of at least parts of the object is determined.

11. Device for determining a spatial structure of an object by means of fluorescence spectroscopy comprising: a) an electromagnetic radiation source for generating an excitation means with a prescribed wavelength range; a1) a second electromagnetic radiation source for generating a second beam with a described wavelength range; b) means for coupling the excitation beam into the object; b1) means for coupling the second beam into the object in such a way as to yield spatial regions with different excitation intensities in the object; c) means for changing the intensity of the excitation beam in such a way as to yield a temporal square pattern of switched-on and off periods; d) means for measuring the time profile (transients) of the emission of the electromagnetic radiation by the object during the switched-on period; e) means for determining different patterns for the time profile of different transients; f) means for adapting the pattern to the measured transient of the emission by means of different amplitudes; g) means for determining the amplitude of that pattern which corresponds to the intensity of the second beam in said spatial region of interest; h) means for selecting the amplitude determined in such a way as the measure of the concentration of the substance in the spatial region of interest; and i) means for coupling the beams into the object in a spatially changed fashion until the spatial structure of at least parts of the object is determined.

* * * * *

UNITED STATES PATENT AND TRADEMARK OFFICE
CERTIFICATE OF CORRECTION

| | | |
|---|---|---|
| PATENT NO. | : 7,817,269 B2 | Page 1 of 1 |
| APPLICATION NO. | : 11/912834 | |
| DATED | : October 19, 2010 | |
| INVENTOR(S) | : Enderlein | |

It is certified that error appears in the above-identified patent and that said Letters Patent is hereby corrected as shown below:

Column 17, line 46, before "the object" insert -- in --

Column 17, line 64, replace "wherein" with -- and --

Signed and Sealed this
Eleventh Day of January, 2011

David J. Kappos
*Director of the United States Patent and Trademark Office*